United States Patent
Shimada et al.

(10) Patent No.: US 9,390,953 B2
(45) Date of Patent: Jul. 12, 2016

(54) SUBSTRATE DAMAGE DETECTION DEVICE, SUBSTRATE TRANSFER ROBOT WITH SUBSTRATE DAMAGE DETECTION DEVICE, AND SUBSTRATE DAMAGE DETECTION METHOD

(71) Applicant: DAIHEN Corporation, Osaka-shi, Osaka (JP)

(72) Inventors: Masaru Shimada, Osaka (JP); Takashi Nagano, Osaka (JP); Takumi Kobayashi, Osaka (JP)

(73) Assignee: DAIHEN Corporation, Osaka (JP)

( * ) Notice: Subject to any disclaimer, the term of this patent is extended or adjusted under 35 U.S.C. 154(b) by 0 days.

(21) Appl. No.: 14/637,607

(22) Filed: Mar. 4, 2015

(65) Prior Publication Data

US 2015/0253258 A1    Sep. 10, 2015

(30) Foreign Application Priority Data

Mar. 6, 2014 (JP) ................................. 2014-043726

(51) Int. Cl.
*G01N 21/88* (2006.01)
*H01L 21/677* (2006.01)
*H01L 21/67* (2006.01)
*G01N 21/95* (2006.01)

(52) U.S. Cl.
CPC ...... *H01L 21/67742* (2013.01); *G01N 21/9501* (2013.01); *H01L 21/67288* (2013.01); *H01L 21/67748* (2013.01); *G01N 2021/9513* (2013.01); *Y10S 901/47* (2013.01)

(58) Field of Classification Search
CPC .. G01N 21/8806; G01N 21/93; G06T 7/0004; B65G 65/005; B25J 9/1697; H01L 21/67288; H01L 21/67742

USPC ............ 356/601–623, 237.1–237.5; 382/141
See application file for complete search history.

(56) References Cited

U.S. PATENT DOCUMENTS

| | | | | |
|---|---|---|---|---|
| 2005/0238222 A1* | 10/2005 | Nakano | ............. | G01N 21/8806 382/151 |
| 2007/0253710 A1* | 11/2007 | Kaneyama | .......... | G03F 7/70341 396/611 |
| 2008/0013820 A1* | 1/2008 | Vertoprakhov | .... | G01N 21/8806 382/141 |
| 2008/0212084 A1* | 9/2008 | Watkins | ............. | G01N 21/9503 356/237.5 |
| 2013/0202387 A1* | 8/2013 | Hiroki | ............... | H01L 21/67161 414/217 |
| 2014/0064886 A1* | 3/2014 | Toshima | ............... | H01L 21/677 414/221 |
| 2014/0202921 A1* | 7/2014 | Babbs | ............... | H01L 21/67775 206/710 |
| 2015/0254827 A1* | 9/2015 | Kobayashi | .............. | G06T 7/001 348/130 |
| 2015/0287625 A1* | 10/2015 | Fujimoto | ............. | G01B 11/002 382/151 |

FOREIGN PATENT DOCUMENTS

JP    2011-139074    7/2011

* cited by examiner

*Primary Examiner* — Hoa Pham
(74) *Attorney, Agent, or Firm* — Hamre, Schumann, Mueller & Larson, P.C.

(57) ABSTRACT

A substrate damage detection device is configured to be mounted to a substrate transfer robot provided with a slidably-movable substrate support. The substrate damage detection device includes an image obtainer and a damage detector. The image obtainer, such as a camera, is configured to obtain an image of the periphery of a substrate placed on the substrate support of the transfer robot. The damage detector is configured to detect damage made to the substrate by using the image of the periphery obtained by the image obtainer.

9 Claims, 11 Drawing Sheets

SUBSTRATE DAMAGE DETECTION DEVICE, SUBSTRATE TRANSFER ROBOT WITH SUBSTRATE DAMAGE DETECTION DEVICE, AND SUBSTRATE DAMAGE DETECTION METHOD

BACKGROUND OF THE INVENTION

1. Field of the Invention

The present invention relates to a substrate damage detection device for detecting damage made to a substrate such as a liquid crystal substrate when the substrate is being transferred by a substrate transfer robot between a plurality of processing chambers in a substrate processing system. The invention also relates to a substrate transfer robot provided with such a substrate damage detection device and to a substrate damage detection method.

2. Description of the Related Art

In a substrate processing system, when a substrate transfer robot transfers a substrate between chambers such as processing chambers, damage to the substrate, such as breakage or cracking, may be made due to e.g. contact of the substrate with a chamber. To remove such a damaged or defective substrate from the substrate processing system, a substrate damage detection device has conventionally been proposed that is configured to detect damage to a substrate caused during when the robot transfers the substrate.

For instance, JP-A-2011-139074 discloses the technique of detecting damage to a substrate by using two optical sensors. The sensors are arranged at opposite sides of an entrance of a processing chamber. Through this entrance, a substrate is introduced into the processing chamber while being carried by a hand of a transfer robot. Each optical sensor includes a light-emitting portion for directing light and a light-receiving portion for receiving light reflected by the substrate when the substrate passes through the entrance. Damage to the substrate is detected based on the amount of light received by the light-receiving portion.

In the technique disclosed in this document, when the transfer robot transfers the substrate into or out of the processing chamber, the two optical sensors move relative to opposite edges of the substrate (the edges extending in parallel to the substrate introducing direction). When a large change is observed in the level of the signal outputted from the sensors, it is determined that damage has been made to the relevant portion of the substrate.

Patent Document 1: JP-A-2011-139074

According to the above-described substrate damage detection technique, detection of damage is possible only with respect to a pair of edges of a rectangular substrate. In other words, the above-described method cannot detect damage that has been made to another pair of edges, i.e., the front and rear edges of the substrate which extend perpendicularly to the substrate introducing direction. Moreover, in the case of a substrate having a shape other than a rectangle, i.e., a circular substrate, for example, the area for which damage detection is possible is more limited.

Further, according to the above-described substrate damage detection technique, a pair of optical sensors need to be arranged at the entrance of each processing chamber. Thus, a relatively large number of optical sensors are necessary.

SUMMARY OF THE INVENTION

The present invention has been conceived under the circumstances described above. It is therefore an object of the present invention to provide a substrate damage detection device that performs damage detection with respect to the entire periphery of a substrate by using a smaller number of sensors. Another object of the present invention is to provide a substrate transfer robot provided with such a substrate damage detection device. Sill another object of the present invention is to provide a substrate damage detection method using such a substrate damage detection device.

According to a first aspect of the present invention, there is provided a substrate damage detection device configured to be mounted to a substrate transfer robot provided with a slidably-movable substrate support. The substrate damage detection device includes: an image obtainer for obtaining an image of a periphery of a substrate placed on the substrate support; and a damage detector for detecting damage to the substrate by using the image obtained by the image obtainer.

Preferably, the image obtainer may include an image capturing unit and an image capture controller. The image capturing unit is movable relative to the substrate along the periphery of the substrate, and the image capture controller is configured to control movement and image capturing operation of the image capturing unit.

Preferably, the image capturing unit may include a camera provided with a line sensor. The camera may be switchable in orientation so as to cause the line sensor to be selectively parallel to one of a first direction and a second direction defined with respect to the substrate support. The first direction and the second direction may be perpendicular to each other.

Preferably, the image capturing unit may include a camera switching unit, a camera support and a camera driver. The camera switching unit is configured to change the orientation of the camera. The camera support is configured to support the camera so as to allow movement of the camera with respect to the substrate support. The camera driver is configured to move the camera.

Preferably, the damage detector may include an image storage for storing a reference image obtained in advance with respect to a substrate with no damage. The damage detector is configured to determine weather the substrate mounted on the substrate support is damaged or not by comparing the image captured by the image capturing unit with the reference image.

According to a second aspect of the present invention, there is provided a substrate transfer robot that includes: a slidably-movable substrate support; a slide driver for sliding the substrate support; a rotation driver for rotating the slide driver; an elevation driver for moving the rotation driver vertically; a controller for controlling the slide driver, the rotation driver and the elevation driver; and a substrate damage detection device according to the first aspect of the present invention.

According to a third aspect of the present invention, there is provided a substrate damage detection method using a substrate transfer robot. By the method, an image capturing unit is provided at a slider driver of the robot for sliding a substrate support of the robot. An image of a periphery of a substrate mounted on the substrate support is obtained while the image capturing unit is being moved relative to the periphery of the substrate. It is determined weather the substrate is damaged or not by the obtained image of the periphery of the substrate.

Preferably, the image capturing unit may include a camera provided with a line sensor, where the camera is switchable in orientation so as to cause the line sensor to be parallel selectively to one of a first direction and a second direction related to the substrate support.

Preferably, the method may further include: setting the camera so as to cause the line sensor to be parallel to the first direction; obtaining an image of a part of the substrate while moving the camera and the substrate relative to each other; setting the camera so as to cause the line sensor to be parallel to the second direction; and obtaining an image of another part of the substrate while moving the camera and the substrate relative to each other.

Preferably, in the method, a relative movement of the camera and the substrate is made by a way in which the substrate is shifted in position while the camera is fixed in position, or by another way in which the camera is shifted in position while the substrate is fixed in position.

In the method, according to an embodiment, the first direction and the second direction are perpendicular to each other. The substrate is in a rectangular form including a first edge, a second edge, a first end and a second end, where the first edge and the second edge are spaced apart from each other in the first direction, and the first end and the second end are spaced apart from each other in the second direction. The relative movement of the camera and the substrate is made by fixing the camera in position and moving the substrate support in the second direction when the line sensor is parallel to the first direction. When the line sensor is parallel to the second direction, then the relative movement of the camera and the substrate is made by fixing the substrate support in position and moving the camera in the first direction.

Preferably, images of the first edge, the second edge, the first end and the second end of the substrate are obtained.

According to the present invention, the substrate damage detection device is provided at the substrate transfer robot. Thus, the substrate processing system can be simplified as compared with the conventional arrangement whereby damage detection is performed by an optical sensor provided at each chamber.

Moreover, according to an embodiment of the present invention, damage detection may be performed with respect to the entire periphery of the substrate placed on the substrate support. That is, the present invention solves the conventional problem that damage detection is possible only with respect to a part of the periphery of the substrate.

Other features and advantages of the present invention will become more apparent from detailed description given below with reference to the accompanying drawings.

DESCRIPTION OF THE PREFERRED EMBODIMENTS

Preferred embodiments of the present invention are described below with reference to the accompanying drawings.

Figure 1:
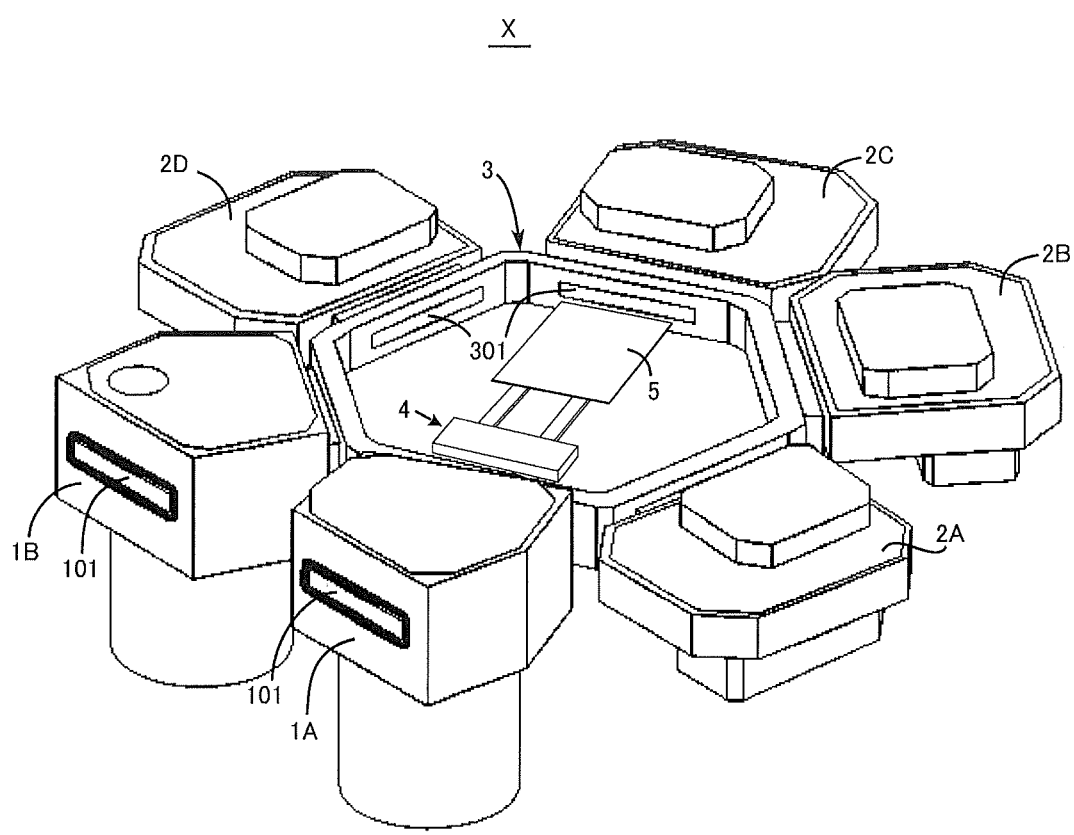
FIG. 1 is a perspective view of an example of a substrate processing system to which a substrate damage detection device according to the present invention is applicable.
Figure 2:
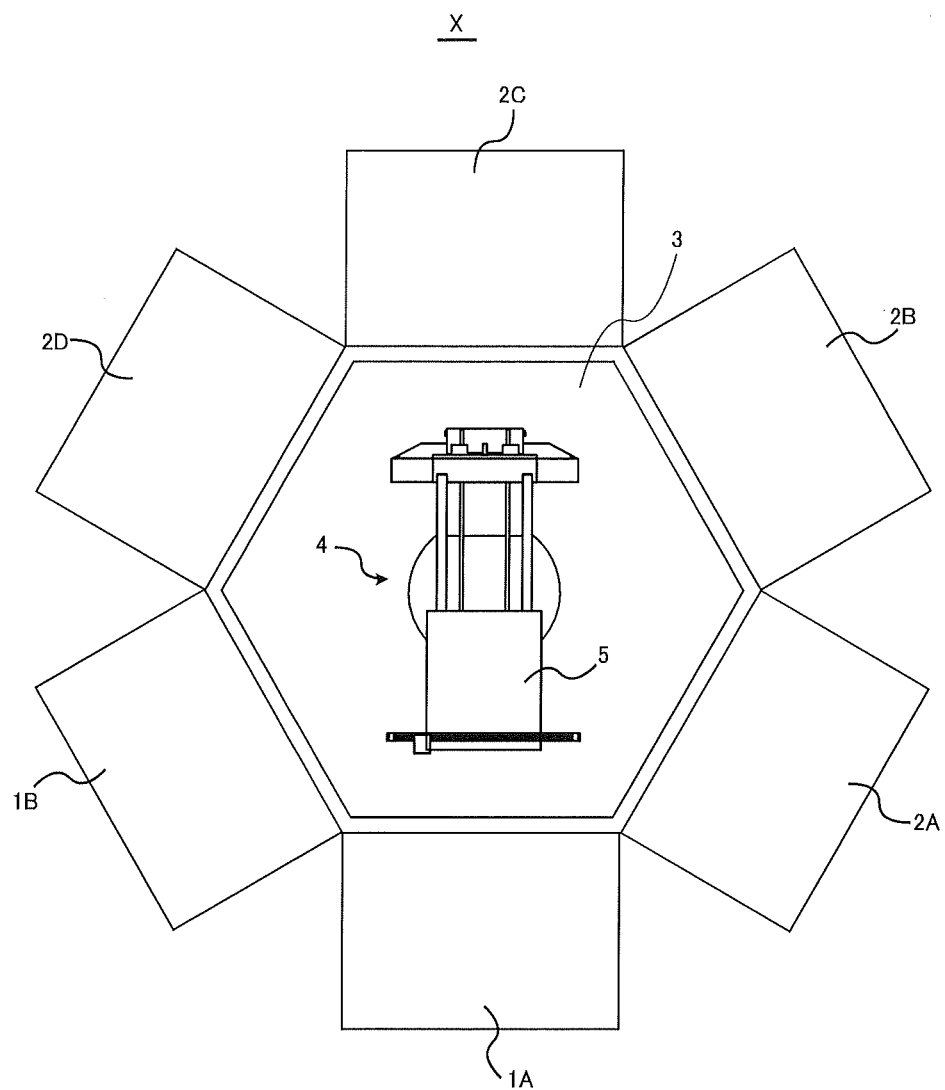
FIG. 2 is a top view of the substrate processing system.

FIG. 1 is a perspective view of an example of a substrate processing system to which a substrate damage detection device according to the present invention is applicable. FIG. 2 is a top view of the substrate processing system. In FIG. 2, the chambers are illustrated as having a rectangular shape for convenience of drawing. This holds true for FIGS. 9-12.

The substrate processing system X illustrated in FIG. 1 includes two load lock chambers 1A and 1B, four processing chambers 2A, 2B, 2C and 2D, a transfer chamber 3, and a substrate transfer robot 4. The two load lock chambers 1A, 1B and the four processing chambers 2A, 2B, 2C, 2D are arranged radially around the transfer chamber 3. As illustrated in FIG. 2, the transfer chamber 3 is hexagonal as viewed in plan. The load lock chambers 1A, 1B are arranged at adjacent two of six sides of the transfer chamber 3, whereas the processing chambers 2A, 2B, 2C, 2D are arranged at the other four of the six sides of the transfer chamber 3. The substrate transfer robot 4 is arranged at the center of the transfer chamber 3. The transfer chamber 3 has six side surfaces each of which is provided with a horizontally-elongated rectangular slot 301 at a predetermined height. The slots 301 are used for introducing or discharging a substrate 5 into or out of the transfer chamber 3.

The processing chambers 2A, 2B, 2C and 2D are provided for performing various processing to the surface of a substrate 5. The substrate 5 may be e.g. a liquid crystal substrate or a semiconductor substrate. Examples of the processing to be performed to the surface of the substrate 5 include thin film formation by CVD (Chemical Vapor Deposition) or PVD (Physical Vapor Deposition), circuit pattern formation by dry etching or lithography, planarization by CMP (Chemical Mechanical Polishing), cleaning by dry cleaning, and junction formation by ion implantation.

The load lock chambers 1A and 1B are used for introducing the substrate 5 from outside the substrate processing system X into the transfer chamber 3 or discharging the substrate 5 from inside the transfer chamber 3 to the outside of the substrate processing system X, while maintaining the interior of the transfer chamber 3 under vacuum. In this embodiment, the load lock chamber 1A is configured as a chamber for introducing the substrate 5, whereas the load lock chamber 1B is configured as a chamber for discharging the substrate 5.

Though not illustrated, outside the load lock chambers 1A, 1B are provided an interface for introducing the substrate 5 into the substrate processing system X or discharging a substrate 5 from the substrate processing system X. Each of the load lock chambers 1A, 1B has an outer side surface provided with a horizontally-elongated rectangular slot 101 for introducing or discharging a substrate into or out of the interface.

The interface includes a substrate transfer robot (different from the substrate transfer robot 4 in the transfer chamber 3) and at least one cassette for storing a plurality of substrates 5. The substrate transfer robot picks up a substrate 5 from the cassette and introduces the substrate 5 into the substrate processing system X through the slot 101 of the load lock chamber 1A. The substrate transfer robot also receives the processed substrate 5 from the load lock chamber 1B through the slot 101 and puts the substrate 5 into the cassette.

The substrate transfer robot 4 receives the substrate 5 from the load lock chamber 1A and transfers the substrate successively to the processing chambers 2A, 2B, 2C and 2D. After the processing in the processing chambers 2A-2D is finished, the substrate transfer robot 4 transfers the substrate 5 to the load lock chamber 1B.

Figure 3:
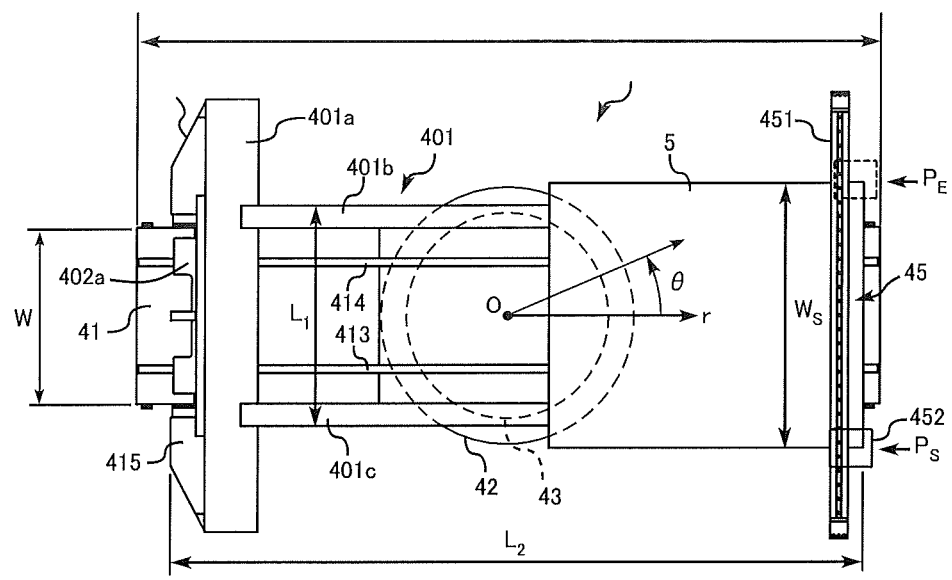
FIG. 3 is a top view of a substrate transfer robot according to the present invention.
Figure 4:
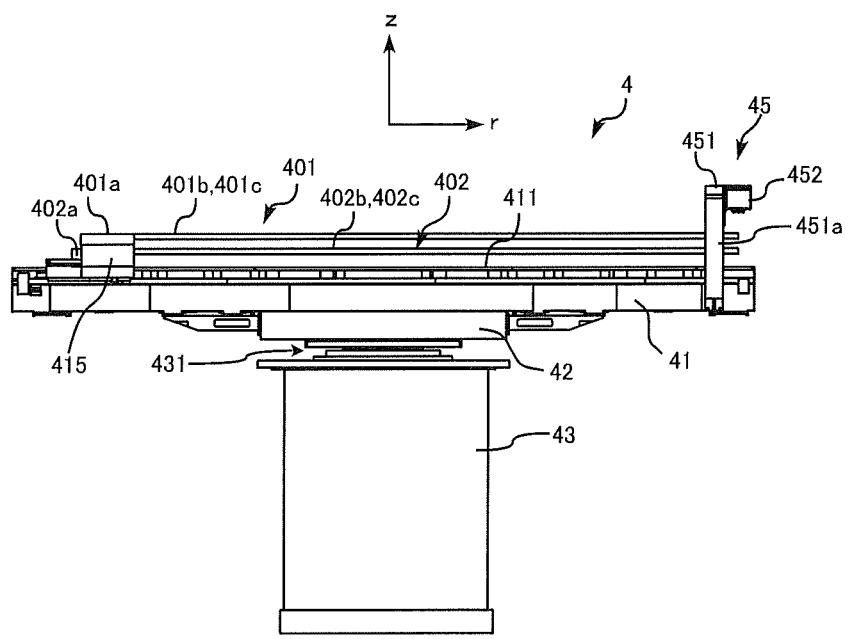
FIG. 4 is a side view of a substrate transfer robot according to the present invention.
Figure 5:
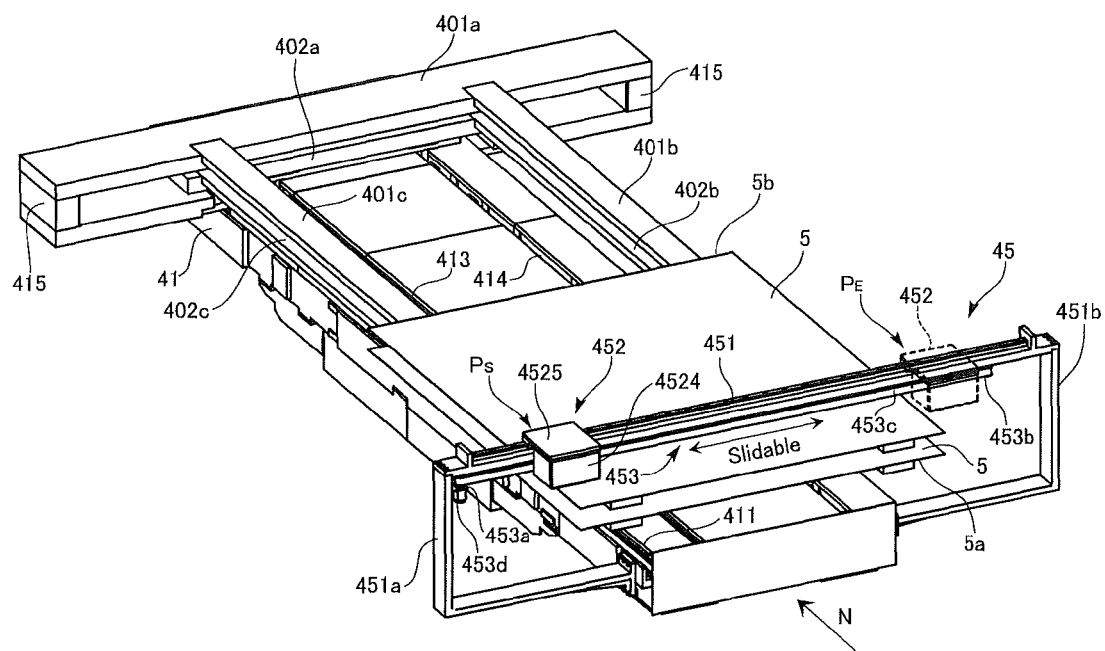
FIG. 5 is a perspective view illustrating a slide driving unit and a substrate damage detection device of a substrate transfer robot.

FIG. 3 is a top view of the substrate transfer robot 4. FIG. 4 is a side view of the substrate transfer robot 4. FIG. 5 is a perspective view illustrating a slide driving unit 41 and a substrate damage detection device 45 of a substrate transfer robot 4.

The substrate transfer robot 4 has two hands, i.e., a first hand 401 and a second hand 402 on which the substrate 5 can be placed. The substrate transfer robot 4 is a cylindrical robot that controls the position of each hand 401, 402 independently based on cylindrical coordinates. As a mechanism for controlling the position of the hands 401 and 402, the substrate transfer robot 4 includes the slide driving unit 41, a rotation driving unit 42, an elevation driving unit 43 and a driver controller 44.

The slide driving unit 41 allows sliding movement (i.e., movement along the r axis of the cylindrical coordinates) of the hands 401 and 402.

The rotation driving unit 42 rotates the slide driving unit 41 to allow rotational movement (i.e., movement along the θ axis of the cylindrical coordinates) of the hands 401 and 402.

The elevation driving unit 43 moves the rotation driving unit 42 and the slide driving unit 41 in the vertical direction to allow vertical movement (i.e., movement along the z axis of the cylindrical coordinates) of the hands 401 and 402.

The driver controller 44 controls operations of the slide driving unit 41, the rotation driving unit 42 and the elevation driving unit 43. The driver controller 44 is apart of the function of the controller 40 (see FIG. 14) that controls the substrate transfer robot 4. Thus, the driver controller 44 is not illustrated in FIGS. 3-5.

The slide driving unit 41 of the substrate transfer robot 4 is provided with a substrate damage detection device 45 for detecting damage or defects made to the substrate 5 that is being transferred by the hand 401 or 402 of the slide driving unit 41.

The substrate transfer robot 4 according to this embodiment is characterized in that it is provided with the substrate damage detection device 45 and configured to detect damage to the substrate 5 by the substrate damage detection device 45 when the substrate 5 is being transferred from the load lock chamber 1A to the processing chamber 2A. The structural features and advantages are mainly described below.

As illustrated in FIG. 4, the elevation driving unit 43 of the substrate transfer robot 4 includes a shaft 431 supported movably in the vertical direction, and a motor coupled to the shaft 431. The shaft 431 moves vertically due to the rotation of the motor. The rotation driving unit 42 of the substrate transfer robot 4 includes a motor having a rotor aligned along the vertical direction. The slide driving unit 41 is connected directly to an end of the rotor.

The motors of the elevation driving unit 43 and rotation driving unit 42 are AC servo motors. The driver controller 44 controls the amount of rotation of the AC servo motor of the elevation driving unit 43 to control the position of the hands 401, 402 along the z axis. The driver controller 44 also controls the amount of rotation of the AC servo motor of the rotation driving unit 42 to control the position of the hands 401, 402 in the direction θ. The cylindrical coordinates (r, θ, z) can be set for the substrate transfer robot 4, for example, with the origin O (0, 0, 0) located at the point where the axis of the shaft 431 of the elevation driving unit 43 intersects a horizontal line passing through the center of the slot 101 of the transfer chamber 1A.

The first hand 401 includes an elongated support plate 401a, and a pair of elongated arms 401b, 401c coupled to the support plate 401a, as shown in FIG. 5. The arm 401b and the arm 401c are at the same distance from the longitudinal center of the support plate 401a. The elongated arms 401b, 401c are each perpendicular to the support plate 401a.

The first hand 401 can hold the rectangular substrate 5 by supporting it from below at the laterally opposite edges of the substrate 5 (edges spaced apart from each other in the width direction) with the arms 401b and 401c. The upper surfaces of front end portions of the arms 401b, 401c constitute a substrate support on which the substrate 5 is to be placed. The distance $L_1$ between the arm 401b and the arm 401c is slightly smaller than the width $W_S$ of the substrate 5.

The second hand 402 is arranged below the first hand 401. Similarly to the first hand 401, the second hand 402 includes an elongated support plate 402a, and a pair of elongated arms 402b, 402c coupled to the support plate 401a. The elongated arms 402b, 402c are perpendicular to the support plate 402a. The distance between the arm 402b and the arm 402c is equal to the distance $L_1$ between the arm 401b and 401c. The upper surfaces of front end portions of the arms 402b, 402c constitute a substrate support on which the substrate 5 is to be placed.

The length of the support plate 402a of the second hand 402 is shorter than that of the support plate 401a of the first hand 401 and slightly longer than the distance $L_1$. The arms 402b and 402c are bonded to opposite ends of the support plate 402a. This arrangement is for the purpose of making it possible to arrange the second hand 402 below the first hand 401 in such a manner that the longitudinal center lines of the first hand 401 and second hand 402 correspond to each other.

The slide driving unit 41 is in the form of a thin parallelepiped and arranged under the second hand 402. As viewed in plan (see FIG. 3), the slide driving unit 41 is in the form of a rectangle having a width W that is slightly shorter than the distance $L_1$ between the arm 402b and the arm 402c (or the distance $L_1$ between the arm 401b and the arm 401c), and a length L slightly longer than the distance $L_2$ from the outer edge of the support plate 402a to the opposite end of the arm 402b or 402c.

The slide driving unit 41 has an upper surface formed with two parallel guide rails, i.e., a guide rail 411 (see FIG. 4) and a guide rail 412 at laterally opposite edges (opposite edges in the width direction). The guide rails 411 and 412 guide the sliding movement of the first hand 401 in the back and forth direction (longitudinal direction of the arms 401b, 401c). The slide driving unit 41 also has two guide rails 413 and 414 (see FIG. 3) arranged inward of the guide rails 411, 412. The guide rails 413 and 414 guide the sliding movement of the second hand 402 in the back and forth direction (longitudinal direction of the arms 402b, 402c).

A slide driver mechanism for the first hand 401 is provided under each of the guide rails 411, 412. A slide driver mechanism for the second hand 402 is provided under each of the guide rails 413, 414.

Figure 6:
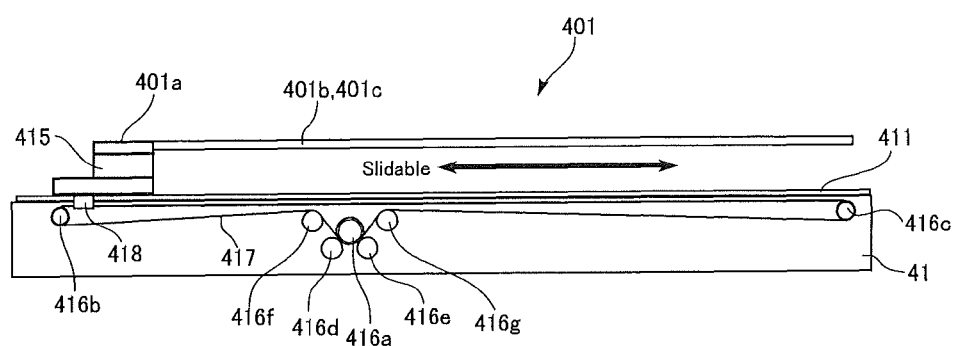
FIG. 6 illustrates the structure of a slide driver mechanism for sliding a hand.

FIG. 6 illustrates the structure of the slide driver mechanism under the guide rail 411. The slide driver mechanism under the guide rail 412 has the same structure.

The slide driver mechanism includes a drive pulley 416a projecting from a side plate under the guide rail 411, a pair of driven pulleys 416b and 416c, an endless belt 417 wound around the drive pulley 416a and the driven pulleys 416b, 416c, and a motor coupled to the shaft of the drive pulley 416a. The motor of the slide driver mechanism is also provided by an AC servo motor.

The driven pulleys 416b and 416c are arranged at opposite ends in the longitudinal direction of the side plate under the guide rail 411. The drive pulley 416a is arranged at an appropriate position between the driven pulley 416b and the driven pulley 416c. Adjacent to the drive pulley 416a are provided a pair of guide pulleys 416d, 416e and a pair of idler pulleys 416f, 416g. The driven pulley 416b is slidably attached so that tension of the endless belt 417 is adjustable by adjusting the position of the driven pulley 416b.

The endless belt 417 is provided with a hand connecting portion 418 for removably connecting the support plate 401a of the first hand 401. The slide driver mechanisms provided for the guide rails 413, 414 have the same structure as that of the slide driver mechanism for the guide rail 411. That is, the endless belt 417 of each slide driver mechanism has a hand connecting portion 418 for removably connecting the support plate 402a of the second hand 402.

The lower surface of the support plate 402a of the second hand 402 is provided with hand attaching portions for removably attaching the second hand 402 to the slide driving unit 41. The hand attaching portions are arranged at positions facing the guide rail 413 and the guide rail 414, respectively. One of the hand attaching portions includes a guide groove that engages with the guide rail 413, and a connecting portion connected to the hand connecting portion 418 of the endless belt 417 under the guide rail 413. The other hand attaching portion also includes a guide groove that engages the guide rail 414, and a connecting portion connected to the hand connecting portion 418 of the endless belt 417 under the guide rail 414. The second hand 402 is attached to the slide driving unit 41 due to engagement of the guide grooves of the hand attaching portions with the guide rails 413, 414 and connection of the connecting portions to the hand connecting portion 418 of each endless belt 417.

The second hand 402 slides along the guide rails 413, 414 within a predetermined area due by rotating the endless belt 417 by the drive pulley 416a of the slide driving unit 41.

Similarly to the second hand 402, the lower surface of the support plate 401a of the first hand 401 is provided with hand attaching portions. Since the second hand 402 is arranged under the first hand 401, the hand attaching portions are arranged so as not to come into contact with the second hand 402. Specifically, L-shaped brackets 415 are provided at opposite ends of the first hand 401 in such a manner that front ends of the brackets 415 extend under the support plate 402a. Hand attaching portions are provided at the respective front ends of the brackets 415.

Similarly to the hand attaching portion provided at the support plate 402a, one of the hand attaching portions provided at the support plate 401a includes a guide groove that engages the guide rail 411, and a connecting portion connected to the hand connecting portion 418 of the endless belt 417 under the guide rail 411. The other hand attaching portion also includes a guide groove that engages the guide rail 412, and a connecting portion connected to the hand connecting portion 418 of the endless belt 417 under the guide rail 412. The first hand 401 is attached to the slide driving unit 41 due to engagement of the guide grooves of the hand attaching portions with the guide rails 411, 412 and connection of the connecting portions to the hand connecting portion of each endless belt 417.

The second hand 401 slides along the guide rails 411, 412 within a predetermined area by rotating the endless belt 417 by the drive pulley 416a of the slide driving unit 41. The area within which the first hand 401 is slidable corresponds to the area within which the second hand 402 is slidable. FIG. 3 illustrates the state where each of the first and the second hands 401, 402 is located at the most retreated position within the slidable range. (This position is hereinafter referred to as "reference position".) The first and the second hands 401, 402 are slidable to the most advanced position within the slidable range, where the substrate 5 is to be transferred between the load lock chambers 1A, 1B or the processing chamber 2A-2D. (This position is hereinafter referred to as "substrate transfer position".) The driver controller 44 controls the amount of rotation of the AC servo motor of the slide driving unit 41 to control the position of the first hand 401 and the second hand 402 in the direction r.

The substrate damage detection device 45 is attached to the front end of the slide driving unit 41. The substrate damage detection device 45 includes a linear guide rail 451, an image capturing unit 452 coupled to the guide rail 451 to be reciprocally slidable along the guide rail 451, a sliding mechanism 453 for sliding the image capturing unit 452 along the guide rail 451, and a damage detecting unit 454. The damage detecting unit 454 controls operations of the image capturing unit 452 and sliding mechanism 453 and detects damage to the substrate 5 based on the image captured by the image capturing unit 452. The damage detecting unit 454 is a part of the function of the controller 40 (see FIG. 14) and hence is not illustrated in FIGS. 3-5.

The guide rail 451 is arranged at a predetermined height so as not to hinder the sliding movement of the first hand 401. The guide rail 451 extends in parallel to the lateral direction (width direction) of the slide driving unit 41. The guide rail 451 is arranged in such a manner that the front edge 5a (see FIG. 8) of the substrate 5 on the first hand 401 (or the second hand 402) overlaps the guide rail 451 as viewed in plan when the first hand 401 (or the second hand 402) is at the reference position.

The guide rail 451 is provided with L-shaped brackets 451a and 451b at its opposite ends. The brackets 451a and 451b couple the guide rail 451 to the slide driving unit 41. Each of the bracket 451a, 451b is attached to the guide rail 451 so that the front end of the bracket reaches a relevant side surface of the slide driving unit 41. The front end of each bracket 451a, 451b is screwed to the side surface of the slide driving unit 41.

As shown in FIG. 5, the upper surface of he guide rail 451 is provided with an elongated rail or rails, and the lower surface of the guide rail 451 is provided with the sliding mechanism 453. The sliding mechanism 453 includes pulleys 453a, 453b rotatably attached to the opposite ends of the guide rail 451, an endless belt 453c wound around the pulleys 453a, 453b, and a motor 453d having a rotor connected to the pulley 453a (the "drive pulley" 453a). The image capturing unit 452 is attached to the endless belt 453c, as explained later.

The endless belt 453c is parallel to the guide rail 451 between the drive pulley 453a and the pulley 453b. When the rotational force of the motor 453d is transmitted to the endless belt 453c via the drive pulley 453a, the endless belt 453c moves linearly between the drive pulley 453a and the pulley 453b. Thus, the image capturing unit 452 attached to the endless belt 453c moves linearly along the guide rail 451.

Figure 7:
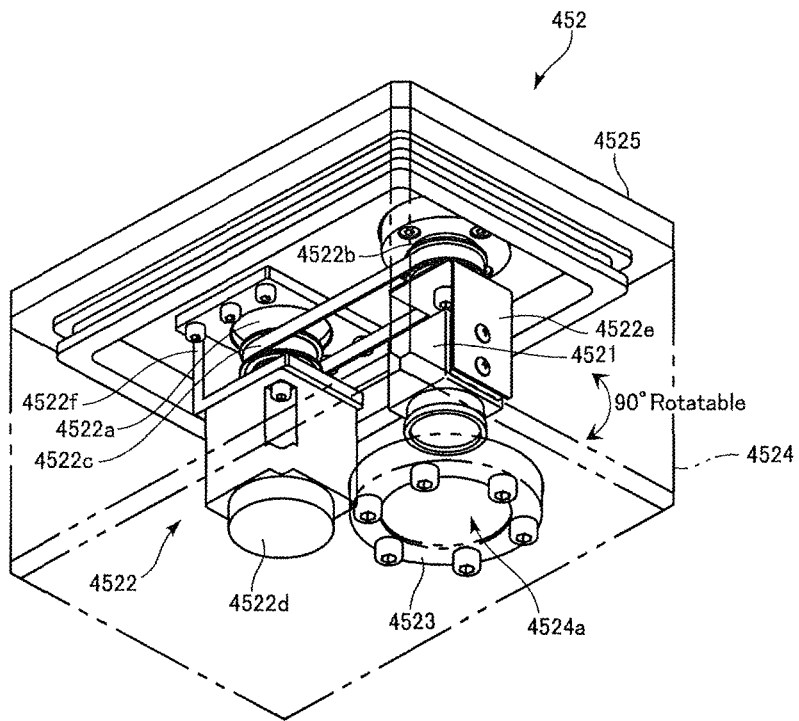
FIG. 7 is a perspective view of an image capturing unit.

As illustrated in FIG. 7, the image capturing unit 452 includes a camera 4521 that includes a monochrome line sensor as an image capturing device, a camera switching unit (or switching mechanism) 4522 for switching the orientation of the camera 4521 (i.e., orientation of the line sensor), a light 4523 for illuminating an object, a housing 4524, and a housing attaching portion 4525. The housing 4524 accommodates the camera 4521, the camera switching unit 4522 and the light 4523. The housing attaching portion 4525 connects the housing 4524 to the guide rail 451 and the slide driving unit 41.

The housing 4524 is in the form of a rectangular parallelepiped having a bottom surface formed with a circular window 4524a. The light 4523 is a circular light including a plurality of light-emitting elements arranged in the form of a ring. The light 4523 is arranged at the window 4524a of the housing 4524. The camera switching unit 4522 includes a pair of pulleys 4522a and 4522b, an endless belt 4522c and a motor 4522d. The pulley 4522a is rotatably arranged at a location facing the window 4524a in the top surface of the housing 4524. The pulley 4522b is arranged at a predetermined distance from the pulley 4522a and rotatably coupled to the top surface of the housing 4524. The endless belt 4522c is wound around the pulley 4522a and the pulley 4522b.

The camera 4521 is coupled to the rotation shaft of the pulley 4522b by using an L-shaped bracket 4522e. The camera 4521 is coupled to the L-shaped bracket 4552f, with its lens facing the window 4524a of the housing 4524 (i.e., with the optical axis of the camera 4521 extending in the vertical direction). The rotor of the motor 4522d, which is fixed to the top surface of the housing 4524 by using an L-shaped bracket 4522f, is coupled to the pulley 4522a.

When the motor 4522d rotates, the rotational force is transmitted to the camera 4521 via the pulleys 4522a, 4522b and the endless belt 4522c, so that the orientation of the camera 4521 changes. The damage detecting unit 454 controls the direction and amount of rotation of the motor 4522d in such a manner that the camera 4521 rotates through +90° from its initial rotational orientation described below.

When the camera 4521 has the initial rotational orientation, the alignment direction of the sensor elements of the line sensor is parallel to the guide rail 451. In this state, capturing an image can be performed by moving the camera 4521 relative to the substrate 5 on the first hand 401 or the second hand 402 in the longitudinal direction of the substrate 5 (i.e., in the movement direction of the first hand 401 or the second hand 402).

The camera 4521 can be rotated clockwise, as viewed from below through the window 4524a. When the camera 4521 is rotated through +90° from the initial rotational orientation, the alignment direction of the sensor elements of the line sensor becomes perpendicular to the guide rail 451. When the camera 4521 has this orientation, capturing an image can be performed by moving the camera 4521 relative to the substrate 5 on the first hand 401 or the second hand 402 in the width direction of the substrate 5 (i.e., the lateral direction of the first hand 401 or the second hand 402). In the description given below, the initial rotational orientation of the camera 4521 is referred to as "first orientation (orientation for longitudinal image capturing)", and the orientation of the camera 4521 after rotated through +90° from the initial rotation orientation is referred to as "second orientation (orientation for lateral image capturing)".

In this embodiment, switching the orientation of the camera 4521 is realized by a driving mechanism using a belt. However, any other switching mechanisms that realizes switching between the first orientation and the second orientation can be employed.

The guide rail 451 defines the range within which the image capturing unit 452 is reciprocally movable. The movable range is determined depending on the size of the substrate 5. Specifically, the movable range is set to a length generally equal to the width Ws of the substrate 5. Viewing the substrate transfer robot 4 from the front (i.e., in the direction indicated by the arrow N in FIG. 5), the left end of the movable range on the guide rail 451 (i.e., the end of the movable range adjacent to the bracket 451a) is defined as a starting position Ps of the forward movement ("forward movement starting position $P_S$"), whereas the right end of the movable range on the guide rail 451 (i.e., the end of the movable range adjacent to the bracket 451b) is defined as an ending position $P_E$ of the forward movement ("forward movement ending position $P_E$"). (The forward movement ending position $P_E$ is also the starting position of the backward movement of the image capturing unit 452.)

Figure 8:
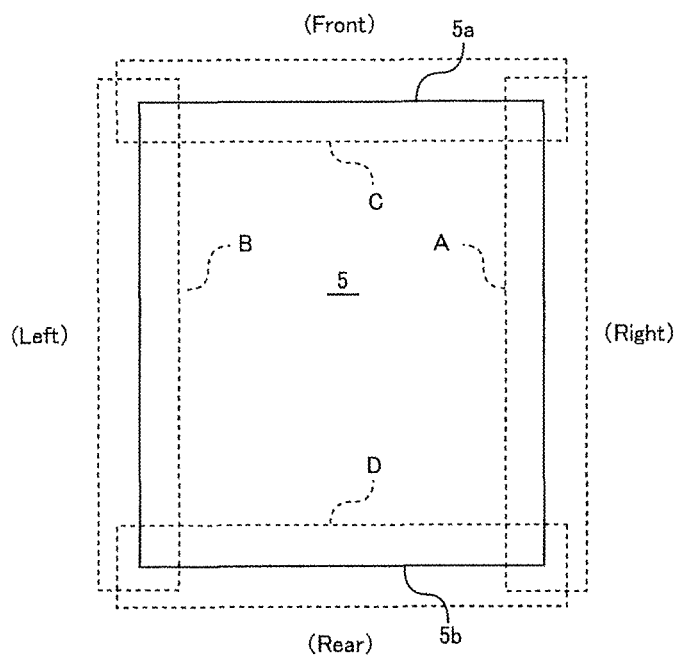
FIG. 8 illustrates regions of a substrate that are to be captured by the image capturing unit.

Consider the situation where the camera 4521 is set at the forward movement starting position Ps while having the first orientation (orientation for longitudinal image capturing). When the first hand 401 or the secondhand 402 on which the substrate 5 is placed is moved in the longitudinal direction, the camera 4521 moves in the longitudinal direction relative to the left edge of the substrate 5. By conducting image capturing using the camera 4521 during this movement, the image $G_A$ (see FIG. 13) of the region A of the substrate 5 depicted in FIG. 8 is obtained.

Consider the situation where the camera 4521 is set at the forward movement ending position $P_E$ while having the first orientation (orientation for longitudinal image capturing). When the first hand 401 or the secondhand 402 on which the substrate 5 is placed is moved in the longitudinal direction, the camera 4521 moves in the longitudinal direction relative to the right edge of the substrate 5. By conducting image capturing using the camera 4521 during this movement, the image $G_B$ of the region B of the substrate 5 depicted in FIG. 8 is obtained.

While the first hand 401 or the second hand 402 on which the substrate 5 is placed is brought to the above-described reference position where the front edge 5a of the substrate 5 is located directly below the guide rail 451, the camera 4521 may have the second orientation (orientation for lateral image capturing). In this situation, by conducting image capturing with the camera 4521 being moved between the forward movement starting position $P_S$ and the forward movement ending position $P_E$, the image $G_C$ of the front region C of the substrate 5 in FIG. 8 is obtained.

Likewise, while the first hand 401 or the second hand 402 on which the substrate 5 is placed is brought to a position where the rear edge 5b (see FIG. 8) of the substrate 5 is located directly below the guide rail 451, the camera 4521 may have the second orientation (orientation for lateral image capturing). In this situation, by conducting image capturing with the camera 4521 being moved between the forward movement starting position $P_S$ and the forward movement ending position $P_E$, the image $G_D$ of the rear region D of the substrate 5 in FIG. 8 is obtained.

Figure 9:
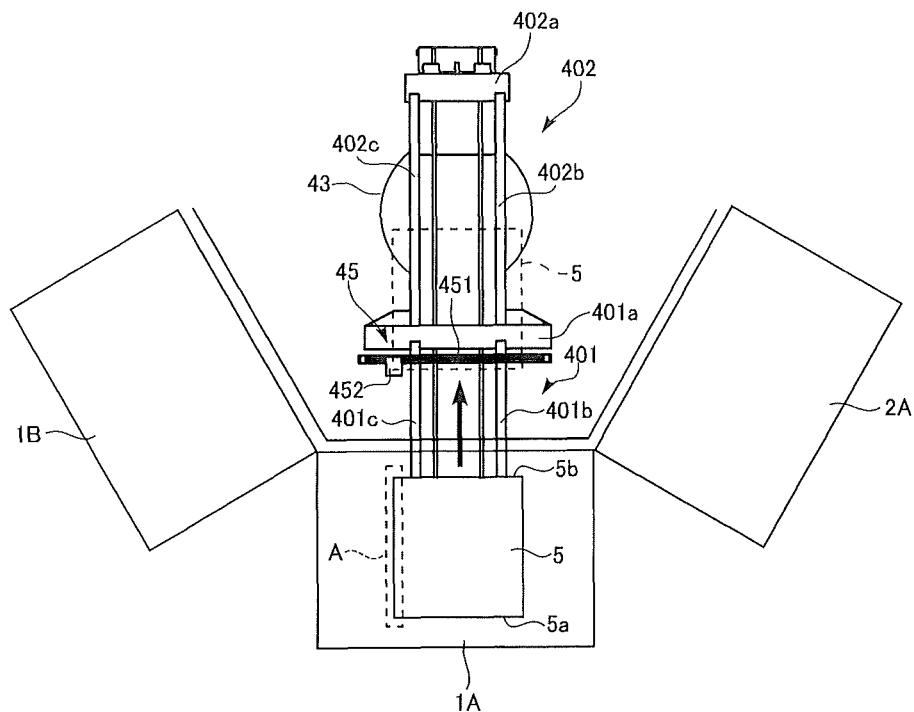
FIG. 9 illustrates the process of capturing an image of the right region of the substrate.

As shown in FIG. 9, after the first hand 401 (or the second hand 402), set at the substrate transfer position, receives the substrate 5 in the load lock chamber 1A, the substrate transfer robot 4 retreats the first hand 401 (or the second hand 402) to the reference position. (Note that the dashed lines in FIG. 9 indicate the position of the substrate 5 when the hand is at the reference position.) When the first hand 401 (or the second hand 402) is being retreated from the substrate transfer position to the reference position, the camera 4521, which has been set at the forward movement starting position $P_S$ and which has the first orientation, is moved relative to the region A of the substrate 5. During this movement, the damage detecting unit 454 causes the camera 4521 to perform image capturing, whereby the image $G_A$ of the region A of the substrate 5 is obtained. After the image capturing, the damage detecting unit 454 detects damage to the region A by performing known pattern matching using the image $G_A$.

Figure 13:
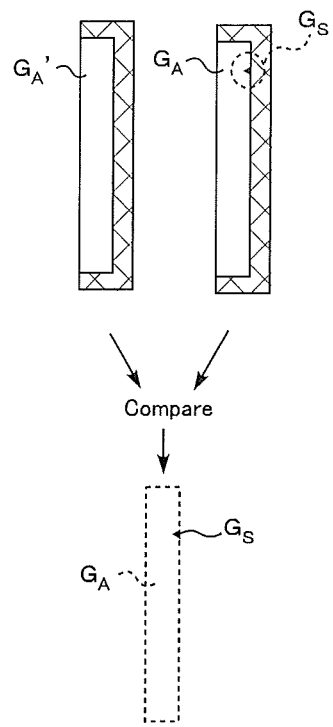
FIG. 13 illustrates pattern matching for detecting damage to the substrate.
Figure 14:
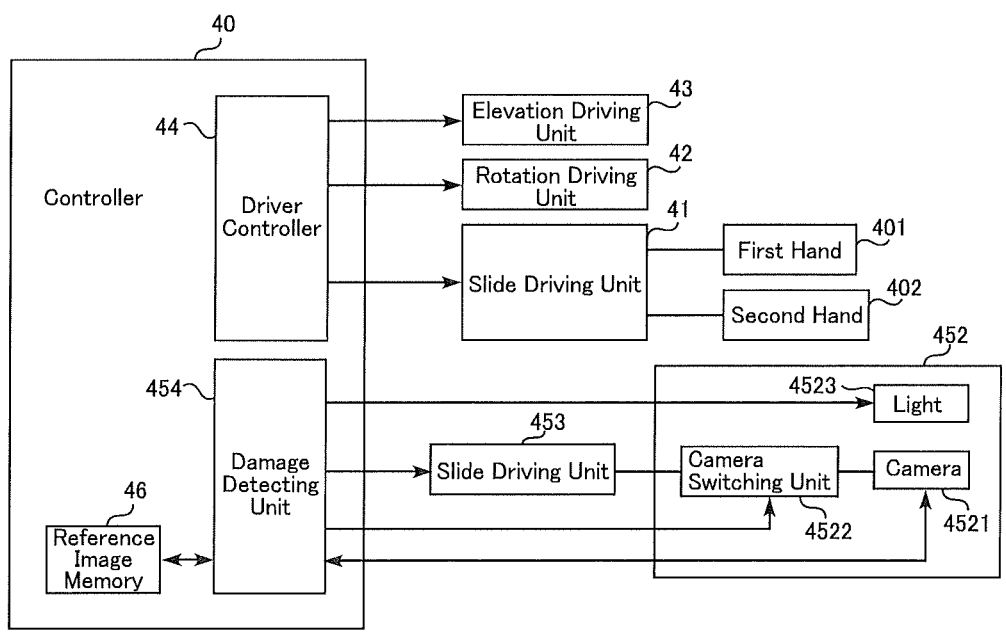
FIG. 14 is a block diagram of an electrical structure related to the substrate damage detection processing.

The damage detecting unit 454 stores, as reference images for pattern matching, images $G_A'$ to $G_D'$ of the substrate 5 with no damage (see the reference image memory 46 in FIG. 14). As illustrated in FIG. 13, the damage detecting unit 454 compares the image $G_A$ captured by the camera 4521 with the reference image $G_A'$. When the image $G_A$ includes a certain size of image $G_S$ that is not included in the image $G_A'$, the damage detecting unit 454 determines the image $G_S$ as the image of damage to the substrate 5.

Figure 10:
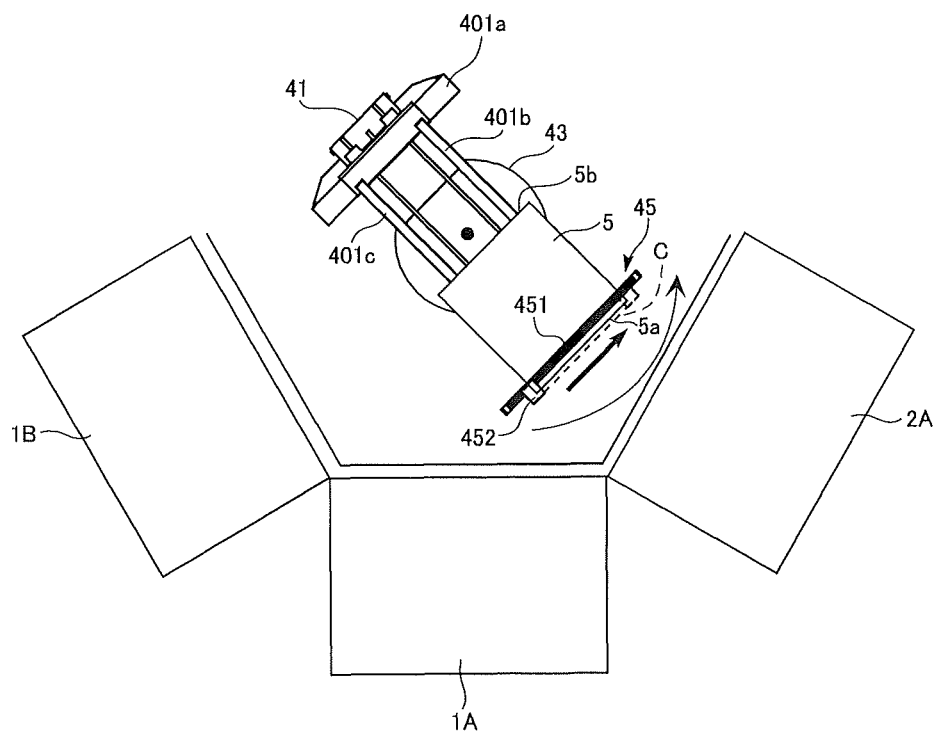
FIG. 10 illustrates the process of capturing an image of the front region of the substrate.

When damage to the region A of the substrate 5 is not detected, the substrate transfer robot 4 turns the slide driving unit 41 so as to face the slot 301 of the processing chamber 2A, while keeping the first hand 401 (or the second hand 402) at the reference position. As illustrated in FIG. 10, while the substrate transfer robot 4 turns the slide driving unit 41, the damage detecting unit 454 switches the camera 4521 to the second orientation (orientation for lateral image capturing) and moves the camera 4521 from the forward movement starting position $P_S$ to the forward movement ending position $P_E$. During this movement, the damage detecting unit 454 causes the camera 4521 to perform image capturing, whereby the image $G_C$ of the region C of the substrate 5 is obtained. After the image capturing, the damage detecting unit 454 detects damage to the region C by performing known pattern matching with respect to the image $G_C$ and the reference image $G_C'$.

When damage to the region C of the substrate 5 is not detected during the rotation of the slide driving unit 41 to the processing chamber 2A, the substrate transfer robot 4 advances the first hand 401 (or the second hand 402) toward the processing chamber 2A. In this advancing movement, the substrate transfer robot 4 stops the first hand 401 (or the second hand 402) when the first hand 401 (or the second hand 402) reaches a predetermined position (the position where the rear edge 5b of the substrate 5 on the hand reaches the image capturing unit 452).

Figure 11:
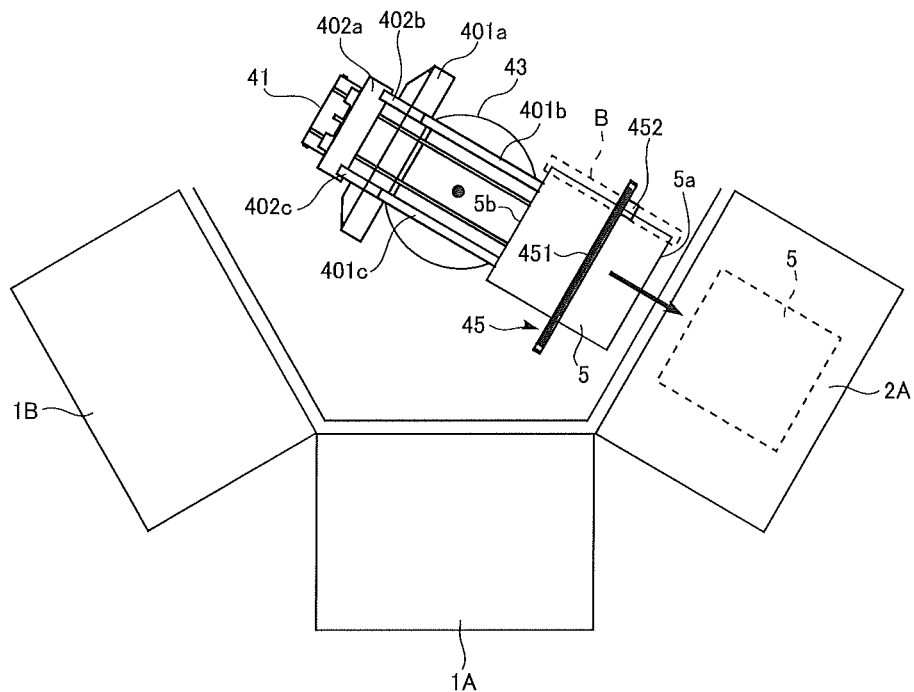
FIG. 11 illustrates the process of capturing an image of the left region of the substrate.
Figure 12:
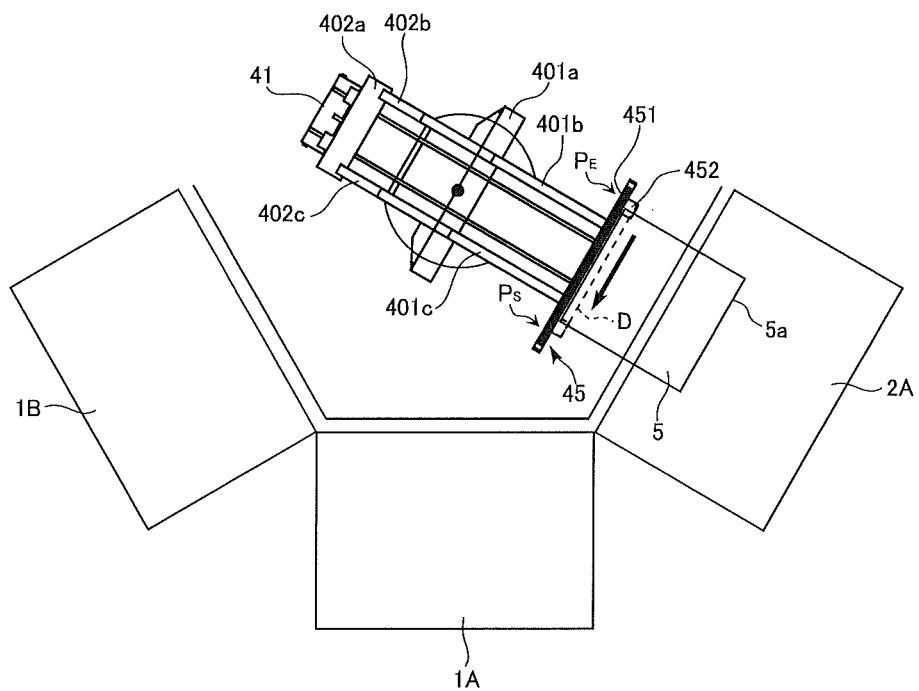
FIG. 12 illustrates the process of capturing an image of the rear region of the substrate.

As illustrated in FIG. 11, the damage detecting unit 454 returns the camera 5421 to the first orientation (orientation for longitudinal image capturing) and causes the camera 4521 to perform image capturing during the advancing movement of the first hand 401 (or the second hand 402) to the predetermined position, whereby the image $G_B$ of the region B of the substrate 5 is obtained. After the image capturing, the damage detecting unit 454 detects damage to the region B by performing known pattern matching with respect to the image $G_B$ and the reference image $G_B'$.

When damage to the region B of the substrate 5 is not detected, the damage detecting unit 454 switches the camera 4521 to the second orientation (orientation for lateral image capturing) and moves the camera 4521 from the forward movement ending position $P_E$ to the forward movement starting position $P_S$. During this movement, the damage detecting unit 454 causes the camera 4521 to perform image capturing, whereby the image $G_D$ of the region D of the substrate 5 is obtained. After the image capturing, the damage detecting unit 454 detects damage to the region D by performing known pattern matching with respect to the image $G_D$ and the reference image $G_D'$.

When damage to the region D of the substrate 5 is not detected, the substrate transfer robot 4 further advances the first hand 401 (or the second hand 402) from the predetermined position to set the substrate 5 in the processing chamber 2A. In this way, damage detection by the damage detecting unit 454 is completed. The substrate transfer robot 4 then takes out the processed substrate 5 from the processing chamber 2A. The substrate transfer robot 4 then successively transfers the substrate 5 into and out of each processing chambers 2B-2D. Thereafter, the substrate transfer robot 4 transfers the substrate 5 into the load lock chamber 1B.

When damage to any of the regions A-D of the substrate 5 is detected, the substrate 5 is determined as a defective. In this case, the substrate transfer robot 4 immediately transfers the substrate 5 to the load lock chamber 1B to discharge the substrate 5 from the substrate processing system X.

FIG. 14 illustrates an electrical structure related to the substrate damage detection processing.

The controller 40 controls operations of the first and the second hands 401 and 402 of the substrate transfer robot 4 and the substrate damage detection operation by the substrate damage detection device 45. The controller 40 includes a microcomputer as the main structural element, which includes a CPU, a ROM, a RAM and an input/output interface connected to each other. The controller 40 executes a substrate transfer program stored in a ROM to control the transfer operation of the substrate 5 by the first hand 401 or the second hand 402 in the substrate processing system X. The controller 40 also executes a substrate damage detection program stored in a ROM to determine whether or not damage has been made to the substrate 5 transferred by the first hand 401 or the second hand 402.

The function achieved by the execution of the substrate transfer program by the controller 40 corresponds to the controlling function by the driver controller 44. The function achieved by the execution of the substrate damage detection program by the controller 40 corresponds to damage detecting function by the damage detecting unit 454. The controller 40 is provided with a reference image memory 46 for storing reference images $G_A'$ to $G_D'$ obtained in advance. For instance, a non-volatile memory such as a flash memory or EEPROM (Electrically Erasable Programmable Read-Only Memory) may be used as the reference image memory 46.

The slide driving unit 41, the rotation driving unit 42, the elevation driving unit 43 and the sliding mechanism 453 are connected to the controller 40.

Referring to the flowcharts of FIGS. 15 and 16 and FIGS. 9-12, the process for detecting damage to the substrate 5 by the substrate damage detection device 45 is explained below. Although the substrate 5 is transferred by the first hand 401 in the example described below, the same damage detection process is performed when the substrate 5 is transferred by the second hand 402.

Figure 15:
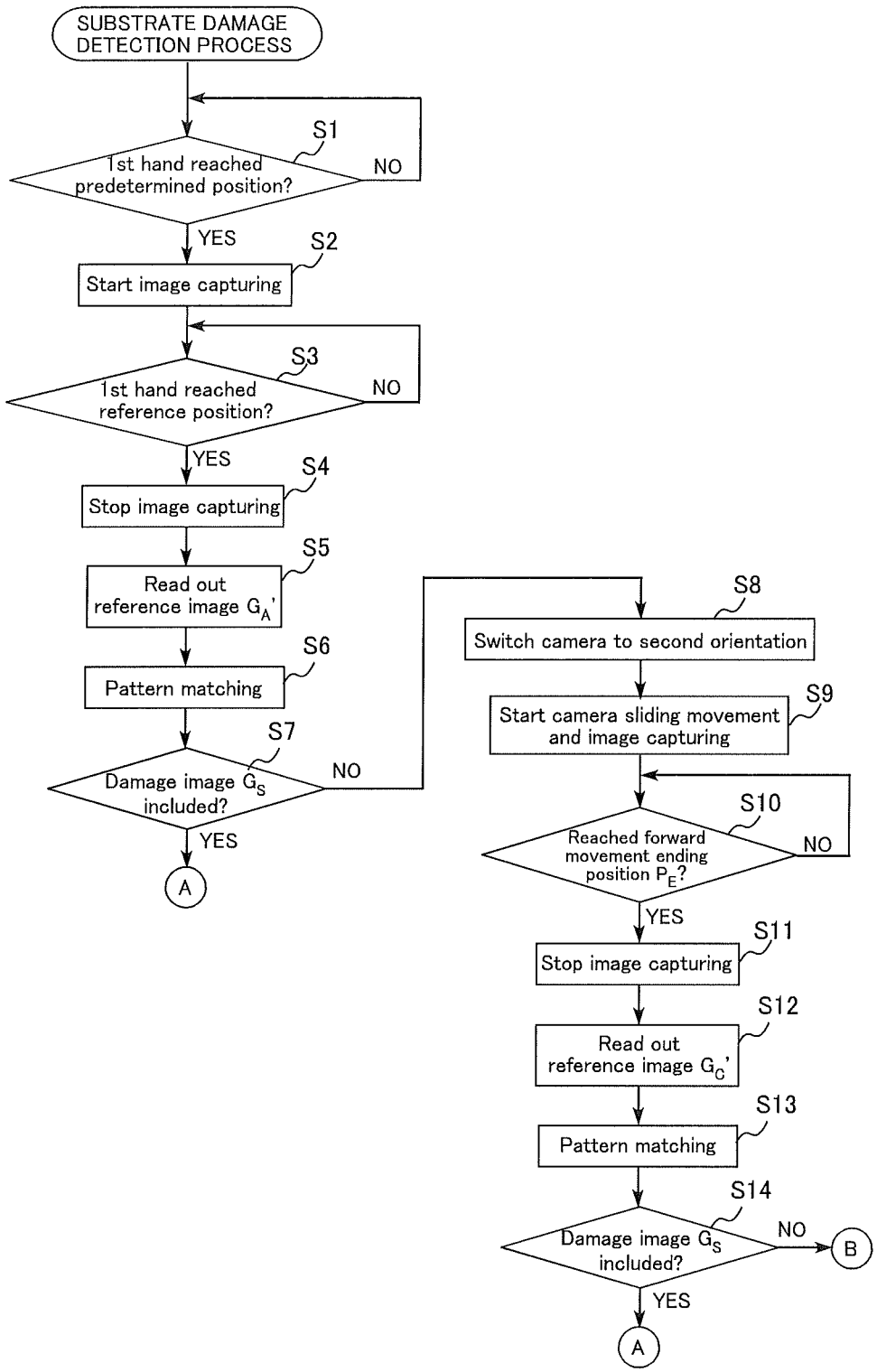
FIG. 15 is a flowchart showing the process for detecting damage to the substrate by the substrate damage detection device.
Figure 16:
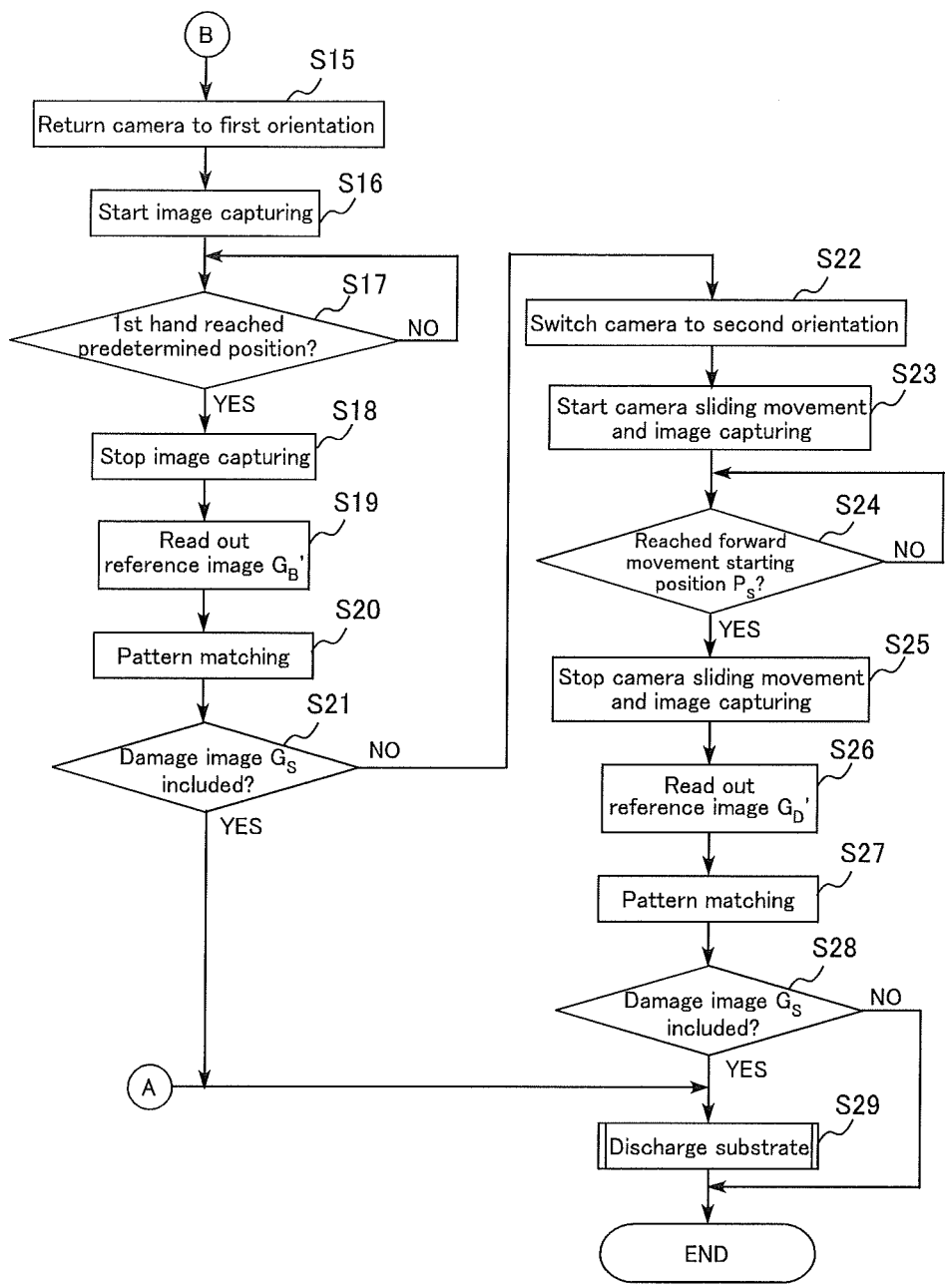
FIG. 16 is a flowchart of the steps that follow the steps in the flowchart of FIG. 15.

In the damage detection process shown in the flow charts of FIGS. 15 and 16, the first hand 401 performs the following operations to transfer the substrate 5:

(a) advancing the first hand 401 to the substrate transfer position in the load lock chamber 1A, elevating the first hand 401, and receiving the substrate 5 (i.e., the substrate 5 is placed on the first hand 401);

(b) retreating the first hand 401, that has received the substrate 5, from the substrate transfer position in the load lock chamber 1A to the reference position;

(c) turning the slide driving unit 41 through +60° so that the first hand 401 faces the slot 301 of the processing chamber 2A;

(d) advancing the first hand 401 to the substrate transfer position in the processing chamber 2A to set the substrate 5 in the processing chamber 2A.

In performing the above-described operation (a) for receiving the substrate 5 by the first hand 401, the substrate transfer robot 4 is oriented in such a manner that the first and the second hands 401, 402 face the slot 301 of the load lock chamber 1A. The first and the second hands 401, 402 are set at the reference position, and the image capturing unit 452 is arranged in such a manner that the camera 4521 is located at the forward movement starting position $P_S$ while having the first orientation (orientation for longitudinal image capturing).

In Steps S1-S7 of the flowchart of FIG. 15, the damage detecting unit 454 performs damage detection with respect to the region A of the substrate 5 (damage detection process of FIG. 9). First, the damage detecting unit 454 determines whether or not the first hand 401, which is being retreated by the slide driving unit 41, has reached a predetermined position (i.e., the position where the rear edge 5b of the substrate 5 on the hand is at the image capturing unit 452) (S1). When the first hand 401 is determined to have reached the predetermined position (S1: YES), the damage detecting unit 454 causes the camera 4521 to start the image capturing operation (S2). Then, the damage detecting unit 454 determines whether or not the first hand 401, which is being retreated by the slide driving unit 41, has reached the reference position (S3). When the first hand 401 is determined to have reached the reference position (S3: YES), the damage detecting unit 454 stops the image capturing operation by the camera 4521 (S4). Note that when the first hand 401 is at the reference position, the front edge 5a of the substrate 5 on the first hand 401 is at the image capturing unit 452.

Then, the damage detecting unit 454 reads out the reference image $G_A'$ from the reference image memory 46 (S5), performs pattern matching by comparing the image $G_A$ captured by the camera 4521 with the reference image $G_A'$ (S6), and determines whether or not any damage image $G_S$ is included in the image $G_A$ (S7). When the damage detecting unit 454 determines that any damage image $G_S$ is included (S7: YES), the substrate 5 is determined as a defective. In this case, the driver controller 44 shifts the process to Step S29 (see in FIG. 16), in which the substrate 5 is discharged from the substrate processing system X. Thus, the substrate damage detection process is finished.

When the damage detecting unit 454 determines that no damage image $G_S$ is included in the image $G_A$ in S7 (S7: NO), the damage detecting unit 454 determines the substrate 5 as a "pass" and continues the substrate damage detection process. In this case, the driver controller 44 shifts to the processing for changing the posture of the substrate transfer robot 4. Specifically, the driver controller 44 causes the rotation driver 43 to rotate the slide driving unit 41 through +60° while keeping the first hand 401 at the reference position. This rotation causes the first hand 401 to face the slot 301 of the processing chamber 2A. During this posture change of the substrate transfer robot 4, or of the first hand 401, the damage detecting unit 454 performs steps S8-S14 of FIG. 15, in order to perform damage detection with respect to the region C of the substrate 5 (damage detection process of FIG. 10).

Specifically, the damage detecting unit 454 switches the camera 4521 to the second orientation (orientation for lateral image capturing) (S8). Then, the damage detecting unit 454 starts the sliding movement of the image capturing unit 452 and the image capturing operation by the camera 4521 (S9). The damage detecting unit 454 determines whether or not the image capturing unit 452 has reached the forward movement ending position $P_E$ (S10). When the image capturing unit 452 is determined to have reached the forward movement ending position $P_E$ (S10: YES), the damage detecting unit 454 stops the sliding movement of the image capturing unit 452 and the image capturing operation by the camera 4521 (S11). Then, the damage detecting unit 454 reads out the reference image $G_C'$ from the reference image memory 46 (S12), performs pattern matching by comparing the image $G_C$ captured by the camera 4521 with the reference image $G_C'$ (S13), and determines whether or not any damage image $G_S$ is included in the image $G_C$ (S14). When the damage detecting unit 454 determines that any damage image $G_S$ is included (S14: YES), the substrate 5 is determined as a defective. In this case, the driver controller 44 shifts the process to Step S29, in which the substrate 5 is discharged from the substrate processing system X. Thus, the substrate damage detection process is finished.

When the damage detecting unit 454 determines that no damage image $G_S$ is included in the image $G_C$ in S14 (S14: NO), the damage detecting unit 454 determines the substrate as a "pass" and continues the substrate damage detection process. In this case, the driver controller 44 shifts to the processing for advancing the first hand 401 from the reference position to the substrate transfer position in the processing chamber 2A. During this advancing movement of the first hand 401, the damage detecting unit 454 performs steps S15-S21 in FIG. 16 to perform damage detection with respect to the region B of the substrate 5 (damage detection process of FIG. 11).

Specifically, the damage detecting unit 454 returns the camera 4521 to the first orientation (orientation for longitudinal image capturing) (S15), and then starts the image capturing operation by the camera 4521 at the same time as the advancing movement of the first hand 401 is started (S16). Then, the damage detecting unit 454 determines whether or not the first hand 401, which is being advanced by the slide driving unit 41, has reached the predetermined position (the position where the rear edge 5b of the substrate 5 on the first hand is at the image capturing unit 452) (S17). When the first hand 401 is determined to have reached the predetermined position (S17: YES), the damage detecting unit 454 stops the image capturing operation by the camera 4521 (S18).

Then, the damage detecting unit 454 reads out the reference image $G_B'$ from the reference image memory 46 (S19), performs pattern matching by comparing the image $G_B$ captured by the camera 4521 with the reference image $G_B'$ (S20), and determines whether or not any damage image $G_S$ is included in the image $G_B$ (S21). When the damage detecting unit 454 determines that any damage image $G_S$ of is included (S21: YES), the substrate 5 is determined as a defective. In this case, the driver controller 44 shifts the process to Step S29, in which the substrate 5 is discharged from the substrate processing system X. Thus, the substrate damage detection process is finished.

When the damage detecting unit 454 determines that no damage image $G_S$ is included in the image $G_B$ in S14 (S21: NO), the damage detecting unit 454 determines the substrate as a "pass" and continues the substrate damage detection process. That is, the damage detecting unit 454 performs steps S22-S28 in FIG. 16 to perform damage detection with respect to the region D of the substrate 5 (damage detection process of FIG. 12). Specifically, the damage detecting unit 454 switches the camera 4521 to the second orientation (orientation for lateral image capturing second) (S22). Then, the damage detecting unit 454 starts the sliding movement of the image capturing unit 452 and the image capturing operation by the camera 4521 (S23). The damage detecting unit 454 determines whether or not the image capturing unit 452 has reached the forward movement starting position $P_S$ (S24). When the image capturing unit 452 is determined to have reached the forward movement starting position $P_S$ (S24: YES), the damage detecting unit 454 stops the sliding movement of the image capturing unit 452 and the image capturing operation by the camera 4521 (S25).

Then, the damage detecting unit 454 reads out the reference image $G_D'$ from the reference image memory 46 (S26), performs pattern matching by comparing the image $G_D$ captured by the camera 4521 with the reference image $G_D'$ (S27), and determines whether or not any damage image $G_S$ is included in the image $G_D$ (S28). When the damage detecting unit 454 determines that any damage image $G_S$ of is included (S28: YES), the substrate 5 is determined as a defective. In this case, the driver controller 44 shifts the process to Step S29, in which the substrate 5 is discharged from the substrate processing system X. Thus, the substrate damage detection process is finished. When the damage detecting unit 454 determines that no damage image $G_S$ is included in the image $G_B$ in S28 (S28: NO), the damage detecting unit 454 determines the substrate as a "pass" and finishes the substrate damage detection process without shifting to the process for discharging the substrate 5.

In the foregoing embodiment, the substrate damage detection process is performed only once during the period after the first hand 401 receives the substrate 5 from the load lock chamber 1A and before the substrate is set in the processing chamber 2A. Unlike this, however, the substrate damage detection process may be performed a plurality of times during the period after the first hand 401 receives the substrate 5 from the load lock chamber 1A and before the substrate 5 is discharged from the substrate processing system X through the load lock chamber 1B.

Although the substrate transfer robot 4 of the dual-hand type is explained in the foregoing embodiment, the present invention is also applicable to a robot of a single hand type.

As described above, according to the present embodiment, the substrate damage detection device 45 is provided at the substrate transfer robot 4. Thus, as compared with the conventional arrangement in which a substrate damage detection device is provided at each chamber of the substrate processing system X, the structure of the system X can be simplified.

Moving the substrate 5 in the longitudinal direction by the first or the second hand 401, 402 realizes moving the camera 4521 of the image capturing unit 452 relative to the substrate 5. Thus, the structure of the image capturing unit 452 is simplified.

Combining the longitudinal movement of the substrate 5 carried by the first or the second hand 401 or 420 and the lateral movement of the camera 4521 in the width direction of the substrate 5 allows the camera 4521 to capture the images $G_A$-$G_D$ of all four sides of the substrate 5. By performing pattern matching using these images $G_A$-$G_D$, damage detection can be performed with respect to all four sides of the substrate 5. Moreover, the images $G_A$-$G_D$ of the four sides of the substrate 5 are captured by using the single camera 4521. Thus, the image capturing unit 452 has a relatively simple structure and the operation to control the image capturing unit 452 is relatively easy.

Although the substrate 5 is transferred by one of the first hand 401 and the second hand 402 in the foregoing embodiment, the damage detection can be achieved when two substrates 5 are simultaneously transferred by the two hands 401 and 402.

Figure 17:
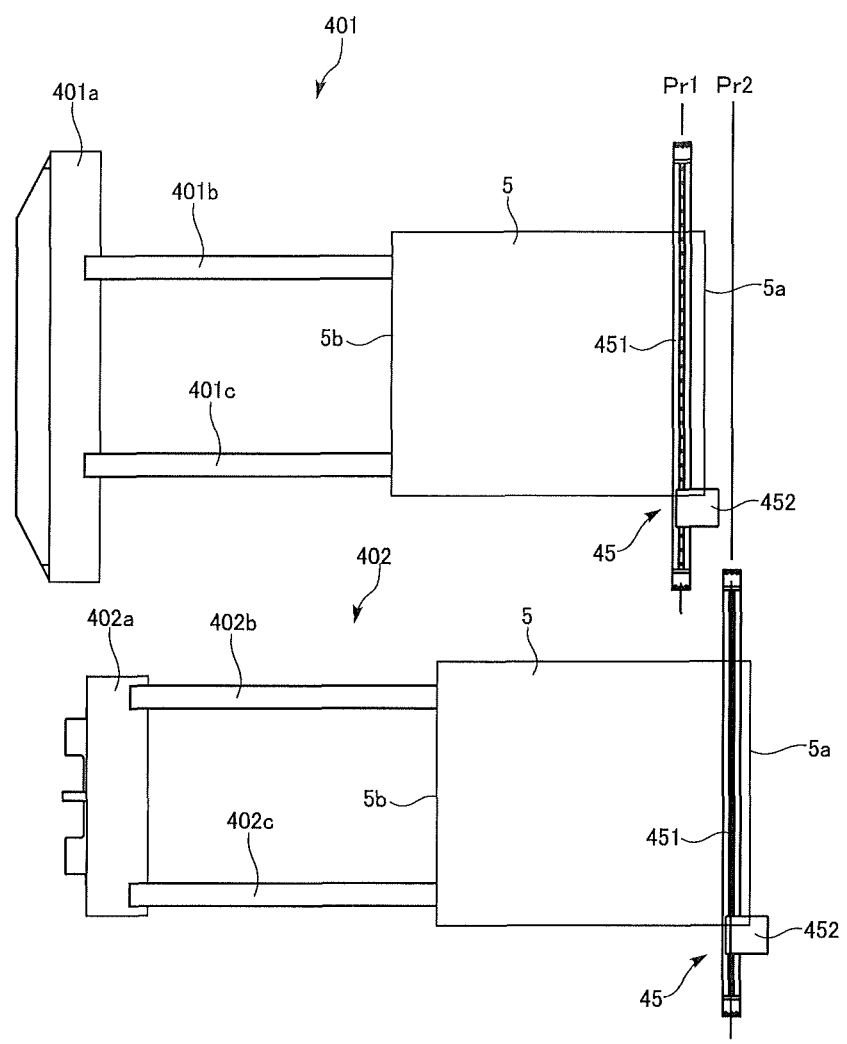
FIG. 17 illustrates a variation for detecting damage to the two substrates placed on two hands.

In this case, as illustrated in FIG. 17, the reference position of the first hand 401 is offset toward the rear side (left in FIG. 17) from the reference position of the second hand 402 (FIG. 17), so that the position $P_{r1}$ of the front edge of the substrate 5 on the first hand 401 (hereinafter referred to as "first substrate 5") does not correspond to the position $P_{r2}$ of the front edge of the substrate 5 on the second hand 402 (hereinafter referred to as "second substrate 5"). The guide rail 451 is attached to the slide driving unit 41 so as to be slidable in the longitudinal direction (right and left direction in FIG. 17).

To detect damage to the first substrate 5 on the first hand 401, the guide rail 451 is set to the position $P_{r1}$. In this state, damage detection with respect to the four sides of the first substrate 5 is performed in the same manner as described above. To detect damage to the second substrate 5 on the second hand 402, the mage capturing unit 452 is set to the position $P_{r2}$. In this state, damage detection with respect to the four sides of the second substrate 5 is performed in the same manner as described above.

According to this arrangement, damage detection can be performed with respect to two substrates 5 without making the structure of the substrate damage detection device 45 complicated.

In the foregoing embodiment, images are captured successively by scanning the substrate 5 with the camera 4521 having a line sensor. Unlike this, images of the regions A-D of the substrate 5 may be captured at the same time by using four area sensors each in the form of a strip. The area sensors are arranged in such a manner as to face the regions A-D of the substrate 5 on the first hand 401 when the first hand 401 is at the reference position. This arrangement simplifies the structure and makes the maintenance easier, because the structure for scanning the substrate 5 with the camera 4521 is not necessary. Moreover, capturing four images at the same time increases the damage detection speed.

Although damage detection is performed with respect to the four sides of the rectangular substrate 5 in the foregoing embodiment, damage detection may be performed only with respect to the two side regions A and B of the substrate 5. In this case, two cameras 4521 fixed to the second orientation are attached to the forward movement starting position $P_S$ and the forward movement ending position $P_E$ of the guide rail 451, respectively. Since this arrangement does not require switching the orientation of the cameras or sliding the cameras, the camera switching unit 4522 and the sliding mechanism 453 as well as the operations to control these mechanisms are unnecessary, which is advantageous.

Although the camera 4521 having a single line sensor is employed in the foregoing embodiment, it is possible to employ a camera including two line sensors of which sensor element alignment directions are perpendicular to each other. In this case, one of the line sensors can be used for longitudinal image capturing of the substrate 5, whereas the other line sensor can be used for lateral image capturing of the substrate 5. This arrangement does not require the camera switching unit 4522 of the image capturing unit 452, which is advantageous.

Although the foregoing embodiment is adapted to detect damage made to four sides of the rectangular substrate, the present invention is applicable to detection of damage made to the periphery of a circular substrate 5. In this case, for instance, the camera 4521 is set in such a manner that its line sensor extends in the radial direction of the substrate 5, and the guide rail 451 is configured to have a circular shape extending along the periphery of the substrate 5. By performing image capturing operation while moving the camera 4521 relative to the periphery of the substrate 5, an image of the periphery of the substrate 5 is obtained. Damage to the periphery of the substrate 5 is detected by performing pattern matching using the obtained image.

The invention claimed is:

1. A substrate damage detection device configured to be mounted to a substrate transfer robot provided with a slidably-movable substrate support, the substrate damage detection device comprising:
   an image obtainer for obtaining an image of a periphery of a substrate placed on the substrate support; and
   a damage detector for detecting damage to the substrate by using the image obtained by the image obtainer,
   wherein the image obtainer includes an image capturing unit and an image capture controller, the image capturing unit being movable relative to the substrate along the periphery of the substrate, the image capture controller being configured to control movement and image capturing operation of the image capturing unit, and
   the image capturing unit comprises a camera including a line sensor, the camera being switchable in orientation so as to cause the line sensor to be selectively parallel to one of a first direction and a second direction defined with respect to the substrate support.

2. The substrate damage detection device according to claim 1, wherein the image capturing unit comprises a camera switching unit, a camera support and a camera driver, wherein the camera switching unit is configured to change the orientation of the camera, the camera support is configured to support the camera so as to allow movement of the camera with respect to the substrate support, and the camera driver is configured to move the camera.

3. The substrate damage detection device according to claim 1, wherein the damage detector comprises an image storage for storing a reference image obtained in advance with respect to a substrate with no damage, and the damage detector is configured to determine whether the substrate mounted on the substrate support is damaged or not by comparing the image captured by the image capturing unit with the reference image.

4. A substrate transfer robot comprising:
   a slidably-movable substrate support;
   a slide driver for sliding the substrate support;
   a rotation driver for rotating the slide driver;
   an elevation driver for moving the rotation driver vertically;
   a controller for controlling the slide driver, the rotation driver and the elevation driver; and
   a substrate damage detection device as set forth in claim 1.

5. A substrate damage detection method using a substrate transfer robot, the method comprising:
   providing an image capturing unit at a slider driver for sliding a substrate support of the substrate transfer robot;
   obtaining an image of a periphery of a substrate mounted on the substrate support while moving the image capturing unit relative to the periphery of the substrate; and
   determining whether the substrate is damaged or not by the obtained image of the periphery,
   wherein the image capturing unit comprises a camera provided with a line sensor, and the camera is switchable in orientation so as to cause the line sensor to be parallel selectively to one of a first direction and a second direction related to the substrate support.

6. The method according to claim 5, further comprising:
   setting the camera so as to cause the line sensor to be parallel to the first direction;
   obtaining an image of a part of the substrate while moving the camera and the substrate relative to each other;
   setting the camera so as to cause the line sensor to be parallel to the second direction; and
   obtaining an image of another part of the substrate while moving the camera and the substrate relative to each other.

7. The method according to claim 6, wherein a relative movement of the camera and the substrate is made by a way in which the substrate is shifted in position while the camera is fixed in position, or by another way in which the camera is shifted in position while the substrate is fixed in position.

8. The method according to claim 7, wherein the first direction and the second direction are perpendicular to each other,
   the substrate is in a rectangular form including a first edge, a second edge, a first end and a second end, the first edge and the second edge being spaced apart from each other in the first direction, the first end and the second end being spaced apart from each other in the second direction,
   the relative movement of the camera and the substrate is made by fixing the camera in position and moving the substrate support in the second direction when the line sensor is parallel to the first direction, and
   the relative movement of the camera and the substrate is made by fixing the substrate support in position and moving the camera in the first direction when the line sensor is parallel to the second direction.

9. The method according to claim 8, wherein images of the first edge, the second edge, the first end and the second end of the substrate are obtained.

* * * * *